(12) United States Patent
Laszlo et al.

(10) Patent No.: US 11,495,333 B2
(45) Date of Patent: Nov. 8, 2022

(54) DATA ANALYTIC APPROACH TO PERSONALIZED QUESTIONNAIRE DEVELOPMENTS

(71) Applicant: X Development LLC, Mountain View, CA (US)

(72) Inventors: Sarah Ann Laszlo, Mountain View, CA (US); Nina Thigpen, Sunnyvale, CA (US); Katherine Elise Link, Palo Alto, CA (US); Vladimir Miskovic, Binghamton, NY (US)

(73) Assignee: X Development LLC, Mountain View, CA (US)

( * ) Notice: Subject to any disclaimer, the term of this patent is extended or adjusted under 35 U.S.C. 154(b) by 359 days.

(21) Appl. No.: 16/902,422

(22) Filed: Jun. 16, 2020

(65) Prior Publication Data

US 2021/0391039 A1 Dec. 16, 2021

(51) Int. Cl.

| | |
|---|---|
| *G06F 16/20* | (2019.01) |
| *G16H 10/20* | (2018.01) |
| *G06F 16/28* | (2019.01) |
| *G16H 50/70* | (2018.01) |
| *G16H 10/60* | (2018.01) |
| *G06F 40/30* | (2020.01) |
| *G16H 50/20* | (2018.01) |
| *G06Q 10/10* | (2012.01) |

(52) U.S. Cl.
CPC .......... *G16H 10/20* (2018.01); *G06F 16/285* (2019.01); *G06F 40/30* (2020.01); *G16H 10/60* (2018.01); *G16H 50/20* (2018.01); *G16H 50/70* (2018.01); *G06Q 10/1053* (2013.01)

(58) Field of Classification Search
CPC ........ F16H 10/20; G16H 10/60; G16H 50/70; G16H 50/20; G06F 16/285; G06F 40/30
See application file for complete search history.

(56) References Cited

U.S. PATENT DOCUMENTS

| | | |
|---|---|---|
| 9,443,205 B2 | 9/2016 | Wall |
| 2018/0189457 A1 | 7/2018 | Plummer et al. |

FOREIGN PATENT DOCUMENTS

| | | |
|---|---|---|
| WO | WO 2018/176083 | 10/2018 |
| WO | WO 2020/000649 | 1/2020 |

*Primary Examiner* — Truong V Vo
(74) *Attorney, Agent, or Firm* — Fish & Richardson P.C.

(57) ABSTRACT

Methods, systems, and apparatus, including computer programs encoded on a computer storage medium, for receiving a plurality of answers to a first set of questions. The actions include generating an adjacency matrix based on the question-answer pairs. The actions include determining a network graph that includes question nodes and edges. The actions include identifying one or more clusters of question nodes by applying a community detection algorithm on the network graph. The actions include determining, for each cluster, i) a cluster centrality and ii) a cluster magnitude. The actions include ranking the clusters based on the cluster centralities and the cluster magnitudes of the one or more clusters. The actions include selecting a second set of questions for the user. And, the actions include causing the questions from the second set of questions to be presented to the user.

20 Claims, 5 Drawing Sheets

DATA ANALYTIC APPROACH TO PERSONALIZED QUESTIONNAIRE DEVELOPMENTS

BACKGROUND

Questionnaires are widely used to categorize applicants, for example, to determine health issues of patients, identify matching jobs for job applicants, determining best way of training students, etc. Usually, questionnaires include a default set of questions that are provided to all applicants, and each applicant is categorized based on the answers that the applicant provides to those questions.

SUMMARY

Implementations of the present disclosure include computer-implemented techniques for identifying and/or generating a set of personalized questions for a user based on the user's unique pattern of responses to prior questions presented to the user. The implementations can be used in a variety of applications. For example implementations can be used in the healthcare industry to diagnose, prescribe, or treat a patient; or in employment industry to determine career aptitude of an applicant, etc.

The implementations provide personalized questions to each user rather than asking the same default questions from all users. The implementations generate the personalized questions for a user by first, asking an initial set of questions from the user, then identifying further questions that are more relevant to the user's answers rather than any default questions, and finally, selecting a set of questions from those identified questions as personalized questions for the user. The implementations can keep modifying the personalized questions until at least one target category such as a health issue, a particular job field, etc. can be identified as a category to which the user belongs.

One innovative aspect of the subject matter described in this specification is embodied in methods that include the actions of receiving, from a user device of a user, a plurality of answers to a first set of questions, each answer in the plurality of answers being associated with one of the questions in the first set of questions and forming a question-answer pair, and where each answer includes an answer value within a range of values. The actions include generating an adjacency matrix based on the question-answer pairs, each element of the adjacency matrix representing correlations between two respective question-answer pairs, the correlation being determined based on answer-values of answers in the two respective question-answer pairs. The actions include determining a network graph that includes question nodes and edges, each question node representing a respective question-answer pair and each edge representing correlations between a pair of question nodes, the edges being derived from elements of the adjacency matrix. The actions include identifying one or more clusters of question nodes by applying a community detection algorithm on the network graph. The actions include determining, for each cluster, i) a cluster centrality and ii) a cluster magnitude, the cluster centrality of a cluster being determined based on the edges within the cluster, and the cluster magnitude for the cluster being determined based on answer-values associated with question nodes in the cluster. The actions include ranking the clusters based on the cluster centralities and the cluster magnitudes of the one or more clusters. The actions include selecting a second set of questions for the user, where the second set of questions has fewer questions than the first set of questions, each question in the second set of questions is associated with a cluster in the one or more clusters, and the questions in the second set of questions are selected based on each question's association with a respective cluster and a cluster rank of the respective cluster. And, the actions include causing the questions from the second set of questions to be presented to the user.

Other embodiments of this and other aspects include corresponding systems, apparatus, and computer programs, configured to perform the actions of the methods, encoded on computer storage devices. A system of one or more computers or other processing devices can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

These and other embodiments may each optionally include one or more of the following features.

In some implementations, the actions include receiving a user answer to a particular question from the second set of questions, updating the adjacency matrix, the network graph, and the one or more clusters based on the user answer to provide updated clusters, ranking the cluster centrality and cluster magnitude of the updated clusters, and selecting a new question to be added to the second set of questions based on the ranking of the updated clusters.

In some implementations, the new question is selected from one of the updated clusters other than the highest-ranked updated cluster.

In some implementations, questions associated with answers that have lower differences in their answer-values are more highly correlated than questions that are associated with answers that have greater differences in their answer-values.

In some implementations, the network graph is a weighted graph, where an edge between two question nodes has a respective weight that is calculated based on a difference between the answer-values of answers in question-answer pairs associated with the two question nodes.

In some implementations, the actions include receiving, from the user, user answers to the second set of questions, and determining a health issue for the user based on the user answers to the first set of questions and the second set of questions. In some implementations, the health issue is determined based on correlations between symptoms of the health issues and question-answer pairs in the highest ranked cluster.

The present implementations provide at least the following technical advantages over prior art. Prior questionnaires usually include a set of default questions that are asked from all users. Since the same default questions is asked from every user, the questionnaires tend to be long. Long questionnaire can cause the users to lose interest and focus, and thus may result in inaccurate user answers. Also, long questionnaires result in a lot of noise in the answers because there are several questions in such questionnaires that are not relevant to the user and can result in misclassification of the user in a target category.

In addition, a default questionnaire may miss some questions that are critical in a user's situation. For example, there may be thousands of questions to be asked to determine a patient's mental health issue. Since asking all of those thousands of questions may be beyond the patient's tolerance, the default questionnaire may include only a random number of questions selected from those thousands of questions without regard to the patient's situation. Although the selected questions may be the most important questions in identifying general health issues, they may easily miss mental health issues that are more critical to the patient and are not categorized as one of those general health issues. As a result the user's mental health issue may easily be mis-classified (or mis-categorized).

The implementations of the present disclosure provide techniques that improve user compliance, data quality, and computational and diagnostic efficiencies. The implementations create questionnaires that are personalized to each user rather than asking default questions from the user. Although the implementations may initially provide a default set of initial questions to a user, the present techniques provide more personalized questions to be asked from the user based on the user's answers to those initial questions and/or to other personalized questions previously provided to the user. As a result, the implementations can determine the categories that the user belongs to in a more efficient manner. The process of providing more efficiently and accurately choosing proper questions for a user reduce the processing load on computing systems. For example, a more efficient questionnaire selection process reduces the number of fetch and reply operations that a system must perform to download questions and upload user responses, thereby, reducing the overall number of data transmissions required to complete a questionnaire. A reduction in data transmissions directly translates to a corresponding improvement in bandwidth usage efficiency. Additionally, since more relevant questions are asked from the user, the user will less likely lose focus and will less likely provide inaccurate answers. Further, more questions associated with the user's specific situation (e.g., health symptoms, job skills, educational interests, etc.) will be asked from the user, which reduces the chance miscategorizing the user in a target category (e.g., health issue, job, training method).

Methods in accordance with the present disclosure may include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Implementations of the present disclosure provide techniques for providing personalized questionnaires to a user. Various implementations are described with respect to the figures presented herein. However, the techniques disclosed herein are not limited to the disclosed figures. Rather, a skilled person in the art may use the ideas behind the present techniques to implement similar systems or methods that provide personalized questionnaires.

Figure 1:
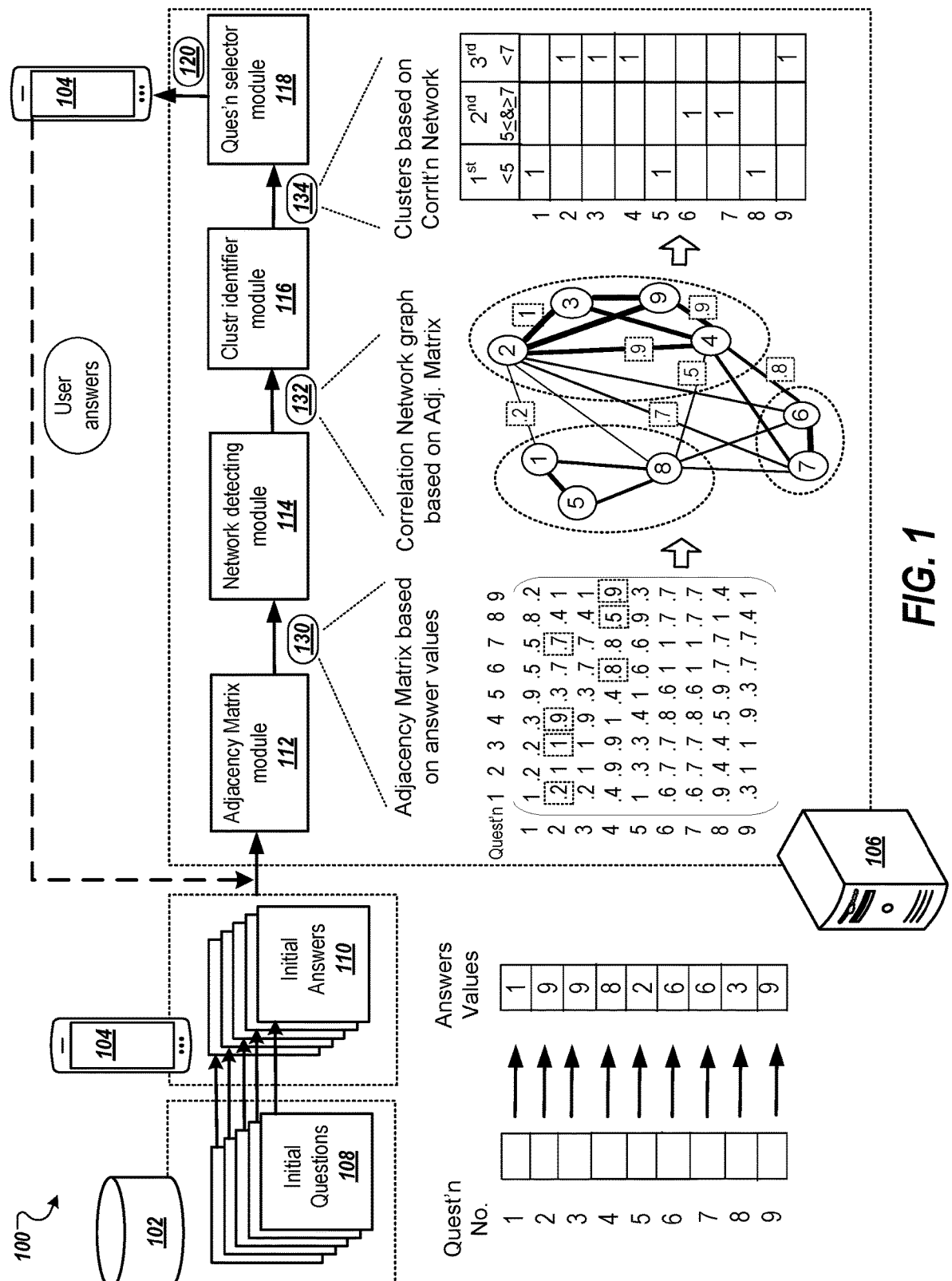
FIG. 1 depicts an example system for developing a personalized questionnaire, according to implementations of the present disclosure.

FIG. 1 depicts an example system 100 for developing a personalized questionnaire for a user of the system 100. The user interacts with the system 100 through a user device 104 to provide an initial set of answers 110 to an initial set of 108. The user device 104 transmits the initial answers 110 to a computing system 106. The computing system 106 uses the initial answers to provides a set of personalized questions 120 to the user.

To do so, the computing system 106 uses the initial answers 110 to determine correlations between questions in the initial set of questions 108. Based on the correlations between the initial questions, the computing system 106 determines one or more clusters of questions 134 in the initial set of questions 108.

Figure 2:
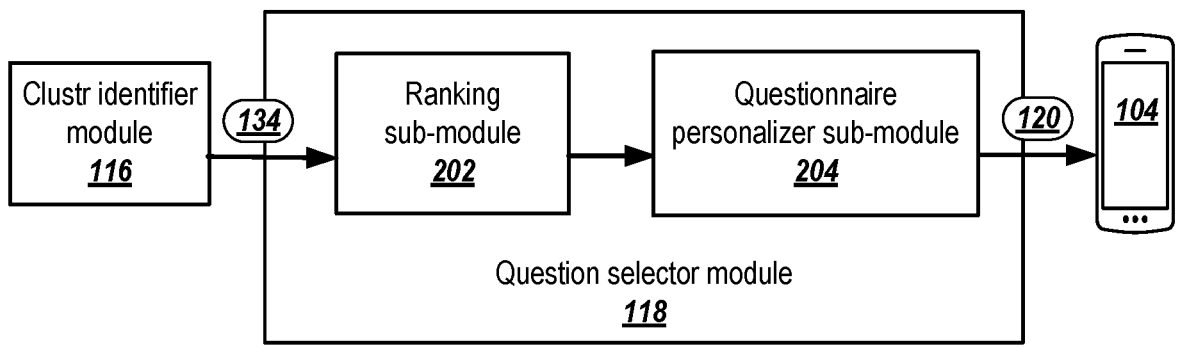
FIG. 2 depicts example sub-modules of an example question selector module of the system depicted in FIG. 1.
Figure 2:
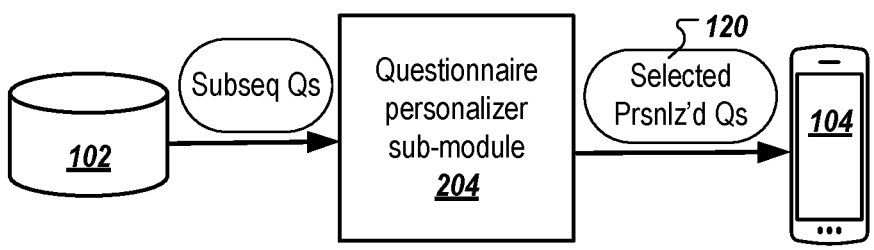

As shown in FIG. 2 and further described below, the computing system 106 ranks the clusters 134 based on each clusters' characteristics. The computing system 106 selects a set of subsequent questions based on (i) correlations between the questions in each cluster and the subsequent questions, and (ii) the cluster ranks. The computing system 106 provides the selected questions to the user device 104 as personalized questions 120.

The correlations between the questions, and the clusters of questions are personalized to the user because the determination of the correlations and forming of the clusters are performed based on the user's initial answers 110. Consequently, since the additional questions are added to each of the personalized clusters and selected for inclusion in the questionnaire based on the ranks of the personalized clusters, the questionnaire is also personalized to the user.

For example, there may be thousands of questions related to health issues such as mental health issues. An initial set of questions, e.g., 20 initial questions, may be selected out of those thousands of questions that span over tens of health issues. The initial questions can be a predetermined set of questions or can be selected by the system 100. The initial questions can be stored as the initial questions 108 in a storage device 102. The system 100 provides those 20 initial questions to a patient and identifies clusters of initial questions based on how likely questions in each cluster touch on the patient's health issues. For example, the system does so by using the patient's initial answers 110 to determine which initial questions are more relevant to the patient's issue, and clusters the more relevant questions (or questions-answer pairs) together. The system may use different set of clusters based on the level of relevancy of the questions in each cluster to the patient. For example, the system may include the most relevant questions in a first cluster, a less relevant set of questions in a second cluster, and the least relevant questions to the user in a third cluster. The procedure to create the clusters is further explained below.

In order to create the clusters of questions from the initial answers 110, the computing system 106 uses one or more modules to determine correlations between questions based on the user's answers to those questions. These modules are depicted in FIG. 1 as an adjacency matrix module 112, a network detecting module 114, and a cluster identifier module 116. Other implementations can have more or less number of modules. For example, in an implementations, the computing system 106 may have no network detecting module 114. In such implementation, the cluster identifier module 116 can generate clusters directly from an adjacency matrix generated by the adjacency matrix module 112. The operation modules 112, 114, 116, and 118 can be provided as one or more computer executable software modules or hardware modules. That is, some or all of the functions of modules 112, 114, 116, and 118 can be provided as a block of code, which upon execution by a processor, causes the processor to perform functions described below. Some or all of the functions modules 112, 114, 116, and 118 can be implemented in electronic circuitry.

The adjacency matrix module 112 forms an adjacency matrix 130 based on question-answer pairs formed from the initial questions 108 and their corresponding initial answers 110. A user may provide the initial answers in form of an answer-value in a range of values (e.g., a number for a question of "in the scale of 1 to 10 how severe is your headache?"). A user may provide the initial answers 110 in form of selecting an answer from multiple choices (e.g., severe, high, neutral, mild, none for a question of "how severe is your headache?"). The computing system 106 can convert the selected answers to answer-values; for example, by assigning values ranging from 4 to 0 to answer choices severe, high, neutral, mild, and none, respectively.

In the example system 100 provided in FIG. 1, the initial questions 108 include 9 questions. The user provides an initial answer in form of an answer-value in the range (or scale) of 0 to 10 to each question.

The adjacency matrix module 112 forms the adjacency matrix 130 based on the initial question-answer pairs. Elements of the adjacency matrix 130 represent correlations between the questions of the question-answer pairs based on the respective answer-values of the answers. For example, questions associated with answers that have lower difference in answer-values can be considered as more correlated than questions that are associated with answers that have greater differences in their answer-values.

In the example depicted in FIG. 1, questions 2 and 3 are highly correlated (depicted by value 1 in the adjacency matrix 130) because the answers to both questions 2 and 3 are 9, which means that the difference between the answer-values of both questions is zero. Questions 2 and 7 have a lower correlation (depicted by value 0.7 in the adjacency matrix) than questions 2 and 3, because the answer-value difference between questions 2 and 7 is three, which is greater than the zero answer-value difference between questions 2 and 3. Questions 2 and 1 have an even greater answer-value differences of 8, and for this reason, questions 1 and 2 have even a lower correlation (depicted by value 0.2 in the adjacency matrix) than questions 2 and 7.

In some implementations, an element $e_{ij}$ of the adjacency matrix can be calculated by $$e_{ij} = 1 - \frac{a_i - a_j}{\text{answer} - \text{value range}} \quad (1)$$

where $a_i$ is answer-value to question i, and $a_j$ is an answer-value to question j. In the depicted example, the answer-value range is 10, resulting in $$e_{21} = 1 - \frac{9-1}{10} = 0.2, e_{23} = 1 - \frac{9-9}{10} = 1, e_{27} = 1 - \frac{9-6}{10} = 0.7.$$

Any other techniques can be used to generate the adjacency matrix based on the answer-values so long as the resulting adjacency matrix 130 represents correlations between the question-answer pairs based on the differences between the answer-values.

The adjacency matrix module 112 provides the generated adjacency matrix 130 to the network detecting module 114. The network detecting module 114 generates a network graph 132 (i.e., a correlation network graph) from the adjacency matrix 130.

Each node of the network graph 132 represents a question-pair or a question associated with a question-answer pair of the adjacency matrix 130. The edges between the network graph nodes are generated based on elements of the adjacency matrix 130.

In the example depicted in FIG. 1, each edge between two nodes of the network graph 132 can have a weight that represents a correlation between two questions associated with the two nodes. For example, the edge between nodes 2 and 3 has a weight of 1 (i.e., $e_{21}$), the edge between nodes 2 and 7 has a weight of 0.7 (i.e., $e_{27}$), and the edge between nodes 2 and 1 has a weight of 0.2 (i.e., $e_{21}$). For an easier comprehension, thickness of the edges between the nodes in network graph 132 are depicted based on the edge weights. For example, the edge between nodes 2 and 3 is thicker than the edge between nodes 2 and 1 because the edge between the former two nodes has a greater weight than the edge between the latter two nodes.

The network detecting module 114 provides the generated network graph 132 to the cluster identifier module 116. The cluster identifier module 116 identifies one or more question clusters 134 by applying a clustering algorithm, such as a community detection algorithm, on the network graph 132. The clustering algorithm identifies clusters of questions based on density of edges between question nodes. Examples of community detection algorithms that the cluster identifier module 116 may use include, but is not limited to, min-cut max-flow algorithm, greedy agglomeration, spectral clustering, walktrap algorithm, and clique percolation.

The cluster identifier module 116 may include nodes that are connected to each other with greater edge weights, in the same cluster. For example, in FIG. 1, nodes associated with questions 1, 5, 8 are grouped in a first cluster, nodes associated with questions 6 and 7 are grouped in a second cluster, and nodes associated with questions 2, 3, 4, and 9 are grouped in a third cluster. In some implementations, an edge must satisfy a specific threshold edge weights to include the two nodes connected by the edge in the same cluster. For example, all edges in each of the three clusters of FIG. 1 have edge weights higher than 0.8.

The computing system 106 ranks the identified clusters 134 to determine which clusters are more relevant to the user—i.e., provides a personalized ranking for the clusters. Based on the ranks of each cluster, the computing system 106 provides to the user a set of questions associated with the clusters—i.e., a set of personalized questions. For example, to do so, the cluster identifier module 116 provides information of the clusters 134 to a question selector module 118. The question selector module 118 uses characteristics of the clusters 134 to rank them. The question selector module 118 then identifies a set of questions that are highly correlated with the questions in the higher ranked clusters, and provides one or more of those identified questions to the user.

The question selector module 118 may itself have multiple sub-modules. FIG. 2 provides two example sub-modules of a question selector module 118: a ranking sub-module 202 and a questionnaire personalizer sub-module 204.

The ranking sub-module 202 receives question clusters 134 from the cluster identifier module 116 and ranks them based on the characteristics of the clusters. In some implementations, the ranking sub-module 202 uses cluster centrality and/or cluster magnitude of each cluster to rank the cluster.

A cluster centrality of a cluster represents the level of correlation between the nodes in the cluster; the more correlated the nodes in a cluster are, the higher the cluster's centrality would be. Cluster centrality of a cluster can be determined based on the number of edges and/or based on the edge weights within the cluster.

In some implementations, the ranking sub-module 202 determines a centrality of a cluster based on an average edge weight of the edges in the cluster. In some implementations, the ranking module determines a centrality of a cluster based on the lowest edge weight in the cluster, where the lowest edge weight represents the lowest correlation between two nodes of the cluster. In some implementations, the ranking module determines a centrality of a cluster based on the greatest edge weight in the cluster, where a greater weight represents a lower correlation between the two nodes of the cluster.

A cluster magnitude of a cluster represents answer-values associated with the question nodes (or question-pair nodes) in the cluster. Magnitude of a cluster can be calculated based on sum of all answer-values associated with the nodes in the cluster.

Section A in FIG. 2 depicts examples of cluster centrality and magnitudes that the ranking sub-module 202 calculated for the first, the second, and the third clusters of clusters 134. In this example, the ranking sub-module 202 assigns a centrality to a cluster by summing of edge weights of the cluster's edges divided by the number of nodes in the cluster. The ranking sub-module 202 also assigns a magnitude to a cluster by averaging answer-value of nodes of the cluster.

For example, the ranking sub-module 202 calculates centrality of the third cluster (associated with question nodes 2, 3, 9, and 4 in FIG. 1) by $$\frac{1+1+1+0.9+0.9+0.9}{4} = 1.425$$

and magnitude of the third cluster by $$\frac{9+9+9+8}{4} = 8.75.$$

Similarly, ranking sub-module 202 assigns centrality of 1 and magnitude of 6 to the second cluster (associated with question nodes 6 and 7), and centrality of 0.86 and magnitude of 2 to the first cluster (associated with questions 1, 5, and 8).

Based on the centrality and the magnitude of each cluster, the ranking sub-module 202 ranks the clusters. In the depicted example, the third cluster receives the highest rank followed by the second cluster and the third cluster because the third cluster has the highest centrality and magnitude.

In some implementations, the ranking sub-module 202 applies a weight to one or more of the cluster characteristics when determining the cluster ranks. For example, the sub-module 202 may apply a greater weight for the cluster centrality than for the cluster magnitude. In such example, because of its greater weight, the cluster centrality will have a more significant effect in determining the cluster rank than the cluster magnitude.

The ranking sub-module 202 provides the cluster ranks to the questionnaire personalizer sub-module 204. The questionnaire personalizer sub-module 204 uses the ranks to select a set of personalized questions 120 and provides the selected questions to the user device 104.

As depicted in section B of FIG. 2, the questionnaire personalizer sub-module 204 can retrieve subsequent questions (e.g., in addition to the initial set of questions 108), for example, from the storage device 102. The subsequent questions can include, for example, thousands of questions that are related to health issues. The questionnaire personalizer sub-module 204 can identify a group of questions associated with each cluster in the clusters 134.

In some implementations, a question may be associated with a particular cluster when the question has a higher correlation to questions in the particular cluster than to questions in any other clusters (in the clusters 134).

In some implementations, the subsequent questions are stored in the storage device 102 as clusters of questions. For example, a question regarding lack of appetite may be stored in the same stored cluster as a question regarding insomnia. The questionnaire personalizer sub-module 204 identifies correlations between the subsequent questions and the questions included in each cluster of clusters 134 based on the stored clusters. For example, if question 2 in the third cluster is about lack of appetite, the questionnaire personalizer sub-module 204 may identify questions about insomnia as being correlated to the third cluster.

In the example depicted in section B of FIG. 2, the questionnaire personalizer sub-module 204 retrieves 400 subsequent questions from the storage device 102, and categorizes those questions based on their correlation to each of the three clusters in clusters 134. The questionnaire personalizer sub-module 204 categorizes questions 1 through 100 as being correlated to (questions of) the first cluster, questions 101 through 150 as being correlate to (questions of) the second cluster, and questions 151 through 400 as being correlated to (questions of) the third cluster.

The questionnaire personalizer sub-module 204 then uses the cluster ranks to select respective number of questions from the subsequent questions associated with each cluster. For example, since the third cluster in FIG. 2 has the highest rank, the questionnaire personalizer sub-module 204 selects a more number of questions (e.g., 6 questions) from the subsequent questions correlated to the third cluster, followed by selecting a less number of questions (e.g., 2 questions) from the subsequent questions correlated to the second cluster, and selecting an even less number of questions (e.g., zero or 1 question) from the subsequent questions correlated to the first cluster.

The questionnaire personalizer sub-module 204 can select questions from the subsequent questions randomly, or based on a particular selection algorithm. In the depicted example, the questionnaire personalizer sub-module 204 randomly selected question numbers 152, 160, 1723, 184, 357, and 398 from among questions 151 through 400 associated with the third cluster, and randomly selected only question numbers 121 and 145 from among questions 101 through 400 associated with the second cluster.

Since the selected questions are selected based on their correlations with the personalized clusters, and since a greater number of questions is selected for the higher-ranked clusters, the selected questions are personalized based on the user's initial answers 110 to the initial questions 108. Thus, the questionnaire personalizer sub-module 204 can provide the selected subsequent questions as personalized questions 120 to the user.

By including questions from the lower ranked clusters (e.g., the second clusters) for inclusion in the personalized questions 120, the computing system 106 keeps evaluating the user's responses to other target categories, but with a less focus on those categories. For example, in FIG. 1, the initial questions 6 and 7 received moderate answer-values 6. However, further questions that focus on health issues correlated to questions 6 and 7 may determine that those health issues are actually important for the user's case even though the user had a moderate symptoms associated with questions 6 and 7.

In some implementations, the number of subsequent questions to be selected as personalized questions for each of the clusters depends on the connectivity between the clusters. The questionnaire personalizer sub-module 204 can include more questions correlated to clusters that are connected to the highest ranked cluster (i.e., third cluster in FIGS. 1 and 2) with higher-weighted edges than questions correlated to clusters that are connected to the highest ranked cluster with lower-weighted edges. For example, looking at either the adjacency matrix 130 or the network graph 132, the lowest edge weight between edges connecting nodes of the third cluster (highest ranked cluster) and the second cluster is 0.7 (which connects question node 2 to question node 7) while the highest edge weight between edges connecting nodes of the third and the first clusters is 0.5 (which connects question node 4 to question node 8). Accordingly, the questionnaire personalizer sub-module 204 selects more questions correlated to the second cluster than questions correlated to the first cluster.

The questions in one cluster may correspond to multiple target categories, e.g., multiple health issues. For example, the third cluster in FIG. 2 may include questions corresponding to both target categories of depression and schizophrenia. In some implementations, the questionnaire personalizer sub-module 204 selects at least one question from two different categories to be included in the personalized questions 120. For example, the questionnaire personalizer sub-module 204 may select at least one question corresponding to depression and at least one question corresponding to schizophrenia from the subsequent questions 151 through 400 associated with the third cluster.

The questionnaire personalizer sub-module 204 can provide the personalized questions 120 to the client device 104 as a set of multiple question, or one question at a time. In some implementations, the computing system 106 receives user answers to the personalized questions 120 and updates the question clusters 134 to dynamically provide relevant and personalized questions to the user.

Figure 3:
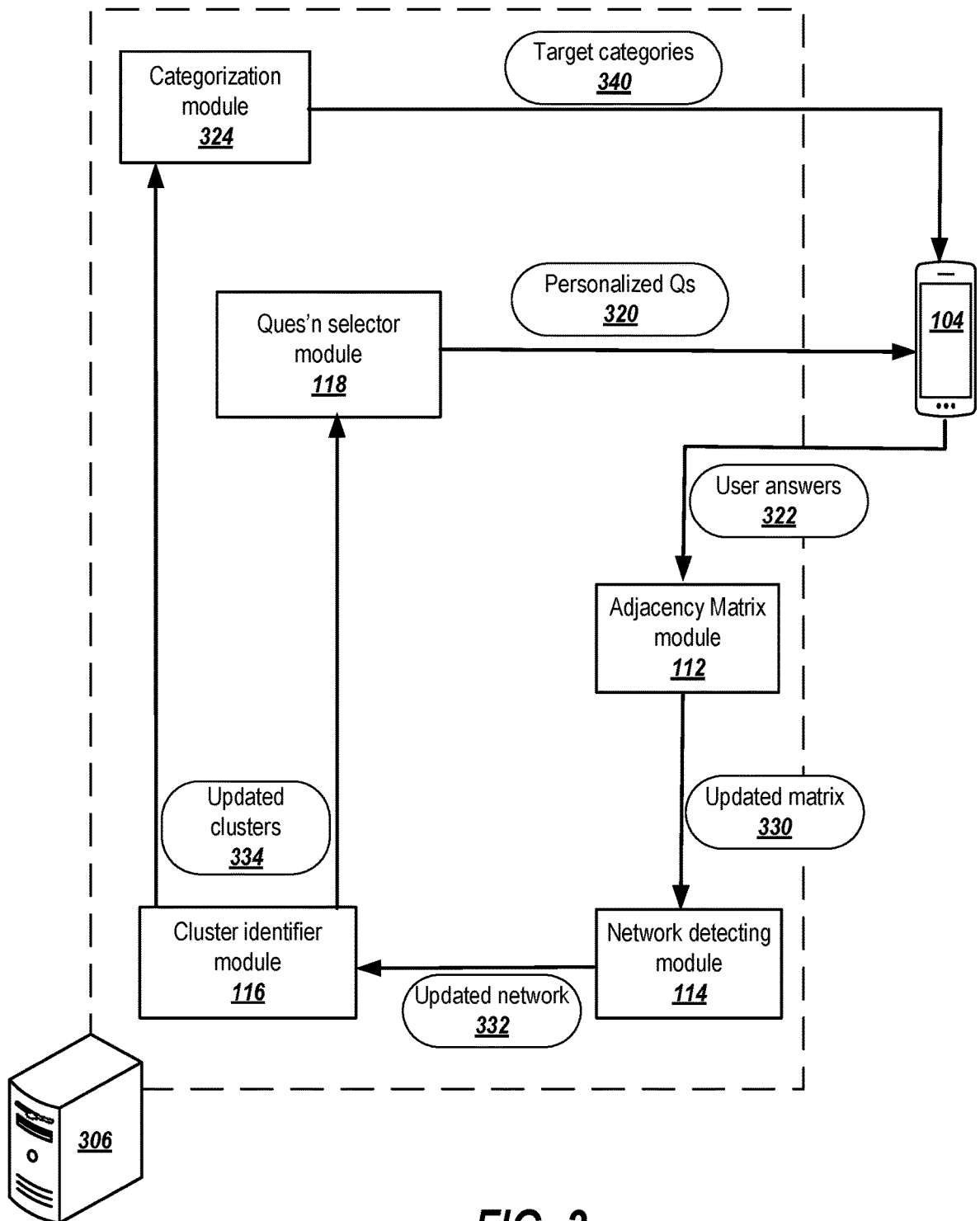
FIG. 3 depicts an example computing system that dynamically provides personalized questions based on answers to prior personalized questions, according to implementations of the present disclosure.

FIG. 3 depicts an example computing system 306 that dynamically updates and provides personalized questions to a user device 104 based on the user's answers to prior questions. The computing system 306 can include one or more of the components of the computing system 106 described above.

The computing system 306 provides personalized questions 320 to the user device 104 and receives the user answers 322 from the user device 104. The computing system 306 can identify/select the personalized questions by executing a process similar to what was explained above in selecting the personalized questions 120.

Upon receiving the user answers 322, the computing system 306 updates the adjacency matrix 130 for the user. To do so, the adjacency matrix module 112 adds additional rows and columns to the previously generated adjacency matrix 130 (see FIG. 1) and the network detecting module 114 adds additional nodes to the network graph 132 to represent new question-answer pairs associated with the personalized questions 320 and the user answers 322.

The adjacency matrix module 112 adds elements to the adjacency matrix 130 to represent correlations between the new question-answer pairs and the previous question-answer pairs (previously presented in the adjacency matrix 130) and obtain the updated matrix 330. The adjacency matrix module 112 provides the updated adjacency matrix 330 to the network detecting module 114. The network detecting module 114 updates the network graph 132 by adding weights associated with the newly added question-answer pair nodes based on the elements of the updated matrix 330, to obtain the updated network graph 332.

The network detecting module 114 provides the updated network graph 332 to the cluster identifier module 116. The cluster identifier module 116 reviews the edges between the nodes in the updated network 332 to update the previous clusters 134 and obtain updated clusters 334. Each cluster in the updated clusters 334 may include the same or different nodes than the previous clusters 134.

For example, referring to FIG. 1, the user may provide an answer with an answer-value 10 to a $10^{th}$ question that was presented to the user as a personalized question 320. In response to receiving this answer-value, the cluster identifier module 116 may change the third cluster to include nodes 2, 3, 9, and 10, and may move node 4 (which had an answer-value of 8) to the second cluster.

In some cases, the cluster identifier module 116 may even create new clusters (e.g., a fourth cluster) that did not exist in the previous clusters 134. For example, the user may provide an answer-value of 10 to five questions presented in the personalized questions 320. In response, the cluster identifier 116 may form a fourth cluster, which includes these additional five questions, in addition to the three clusters in the previous clusters 134. In some cases, the cluster identifier module 116 may reform a previous cluster 134 by moving the cluster's nodes to other clusters.

The cluster identifier 116 provides the updated clusters 334 to the question selector module 118. The question selector module 118 ranks the updated clusters 334 and select new personalized questions 320 to be provided to the user device 104. One or more questions in the newly selected personalized questions can be the same as questions previously presented to the user. For example, the user may be asked again about severity of their headache.

The computing system 306 may repeat the cycle of providing personalized questions 320 to and receiving user answers 322 from the user device 104 until at least one target category (e.g., a health issue, a job that suits the user, etc.) can be determined for the user. Once the computing system 306 stops the cycle, the cluster identifier module 116 provides the updated clusters 334 to a categorization module 324 of the computing system 306. The categorization module 324 can identify at least one target category 340 that the user belongs to. The categorization module 324 can provide the identified target category(ies), to the user device 104, and/or communicate the identified target category(ies) 340 to another user device, e.g., user device of a health care provider, an employer, a trainer, etc.

In some implementations, the computing system 306 stops the cycle (e.g., stops providing more personalized questions 320 to the user device 104) when the computing system confidently determines that the user belongs to at least one of the target categories. The system can be confident when correlations between the user's answers 322 and questions related to the determined target category is high enough to satisfy a threshold confidence value.

In some implementations, the computing system 306 stops the cycle after asking a predetermined number of personalized questions from the user. In such implementations, the computing system 306 may provide one or more of the target categories that are most highly correlated to the user answers as the categories that the user belongs to.

The computing system 306 can determine that the user belongs to a target category based on the question-answer pairs in the most highly ranked cluster. Since each question in any of the clusters has correlations to one or more target categories, target categories that have the highest correlations to the questions in the most highly ranked cluster can be selected as the categories that the user belongs to.

For example, assuming there are four question clusters in the updated clusters 334, and the fourth cluster has the highest rank, the categorization module 324 reviews the questions stored in the fourth cluster and determines correlations between those questions with predetermined target categories to provide one or more of the most relevant target categories (340). For example, if there are thirty question nodes in the fourth cluster, and fifteen of those question nodes correlate to depression, twelve of those question nodes correlate to grief, and five of those question nodes correlate to hormonal issues, the categorization module 324 may determine that the user is suffering from either depression or grief, as the health issues with the highest correlations to the highest rank cluster. Note that some questions can be correlated to more than one target category. For example, (questions about) lack of sleep may be correlated to both grief and hormonal issues.

Figure 4:
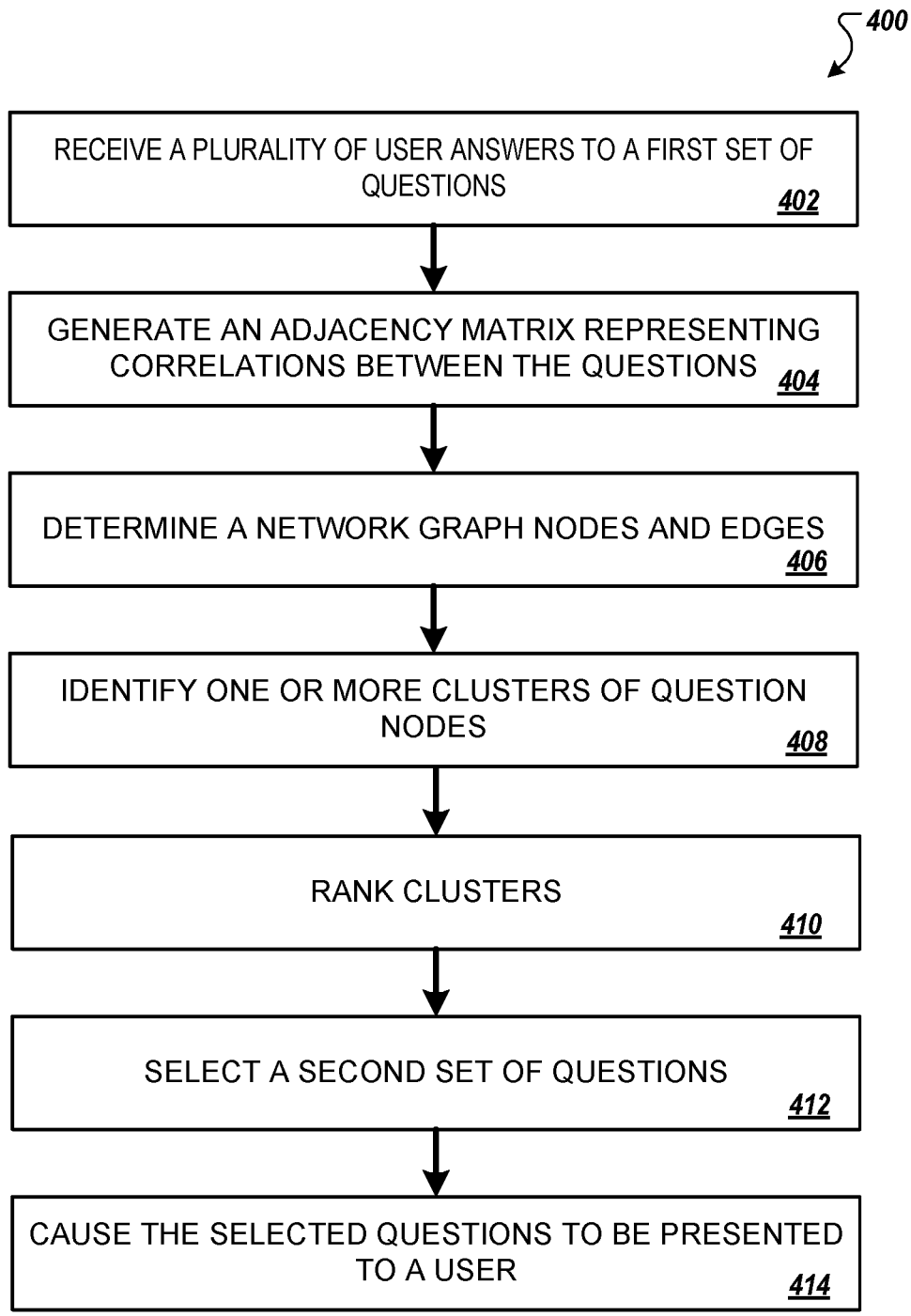
FIG. 4 depicts an example personalized questionnaire development process according to implementations of the present disclosure.

FIG. 4 depicts an example personalized questionnaire development process 400 according to implementations of the present disclosure. The process 400 can be executed by a computing systems, for example, the computing system 106 or 306.

The computing system receives a plurality of user answers to a first set of questions (402), e.g., the initial questions 108 in FIG. 1. Each answer in the plurality of answers is associated with one of the questions in the first set of questions. Accordingly, a respective question-answer pair is formed by each question in the first set of questions and their corresponding answers. Each answer can include an answer-value within a range of values. For example, the answers 110 in FIG. 1 range between 0 and 10.

The computing system generates an adjacency matrix representing correlations between the question in the first set of questions based on the received answers (404). For example, the computing system 106 generates the adjacency matrix 130 based on the initial answers 110. The rows of the adjacency matrix represent the question-answer pairs, and the elements of the matrix represent correlations between the question-answer pairs.

The computing system determines a network graph of question nodes and edges (406). Each question node represents a respective question-answer pair and each edge represents correlations between a pair of question nodes. The edges are derived from the adjacency matrix. For example, the edges in the network graph 132 in FIG. 1 have weights that correspond to the elements of the adjacency matrix 130.

In some implementations, the computing system uses creates a Gaussian graphical model, such as a graphical LASSO, as the network graph. The created network graph can be a partial correlation network.

The edge weights of the network graph's edges can be ranged in any predetermined range. While in the example depicted in FIG. 1 the edge weights range between 0 and 1, the edge weights in another example can range between −1 and 1. A negative edge weight can represent a negative correlation, and a positive edge weight can present a positive correlation between the nodes that the edge connect to each other. For example, (questions related to) stomach ache may be negatively correlated to (questions related to) oversleeping, but may be positively correlated to (questions related to) loss of appetite.

The computing system uses the network graph and/or the adjacency matrix to identify one or more cluster of question nodes (408). The computing system may identify the clusters by applying a community detection algorithm on the question-answer pairs and their correlations. For example, the computing system 106 in FIG. 1 identifies the clusters 134 based on the nodes and edges of the network graph 132.

The computing system ranks the clusters based on cluster characteristics (410). For example the computing system 106 determines cluster centrality and cluster magnitude of each cluster and uses the centrality and magnitude of each cluster to determine the cluster ranks (see FIG. 2).

The computing system selects a second set of questions for the user (412). The second set of questions may have fewer questions than the first set of questions. Each question in the second set of questions is associated with a respective cluster identified at 408. The questions in the second set of questions are selected based on the ranking of the clusters. For example, for example, in FIG. 2, the second set of questions is depicted as "selected personalized questions." The most number of questions in the second set of questions are selected from questions associated with the highest ranked cluster (i.e., the third cluster) followed by the questions associated with the second-highest ranked cluster (i.e., the second cluster). Questions associated with the lowest-ranked cluster (i.e., the first cluster) have the lowest number of questions in the second set of questions.

The computing system causes the selected questions in the second set of questions to be presented to a user (414). For example, the computing system may be in communication with a user device, as depicted in FIG. 1 or 3, and can send the second set of questions to the user device for presentation.

Figure 5:
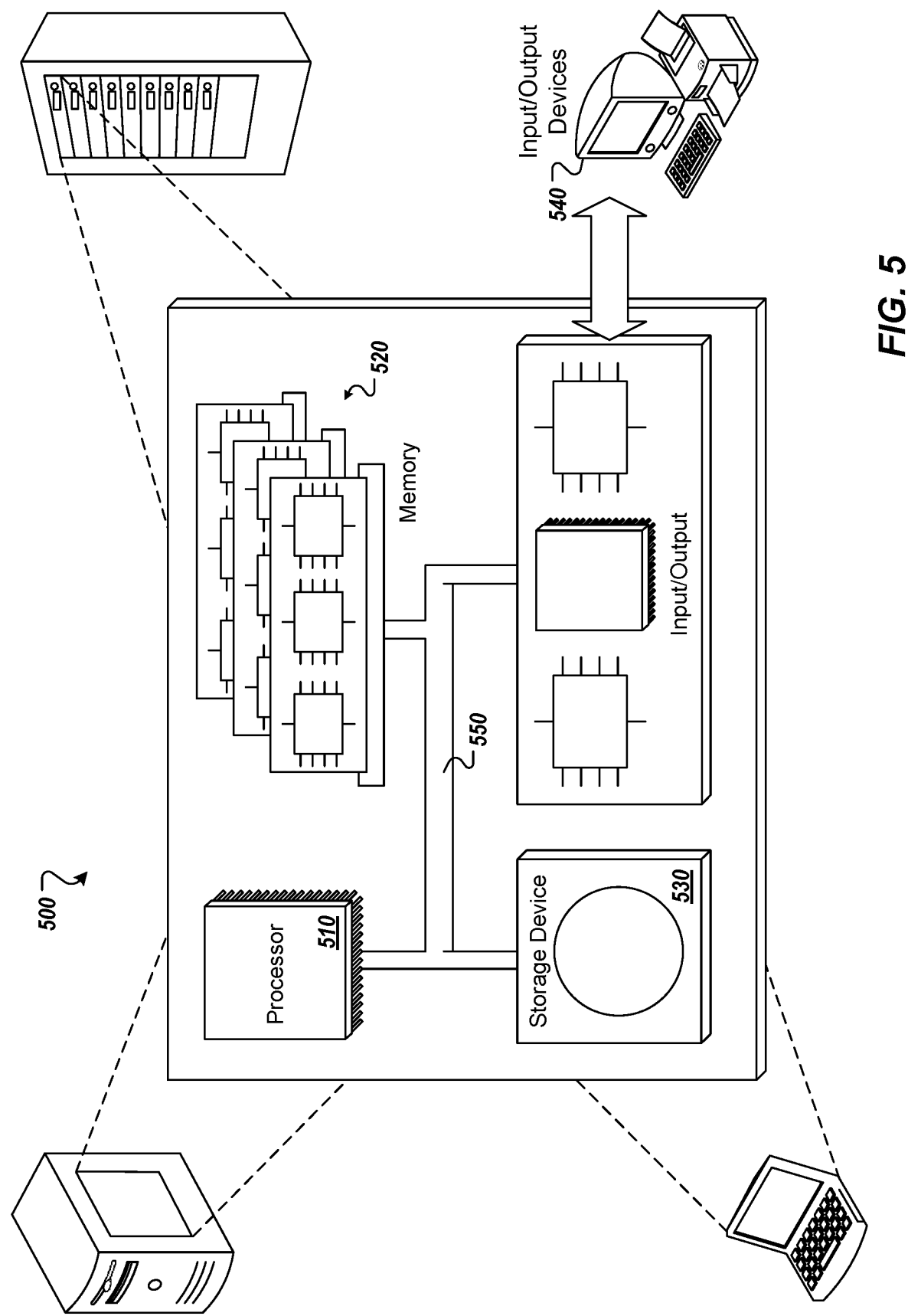
FIG. 5 depicts a schematic illustration of an example computer system that can be used to execute implementations of the present disclosure.

FIG. 5 depicts a schematic diagram of an example computing system 500. The system 500 may be the system 100 presented in FIG. 1. The system 500 can be used to perform the operations described with regard to one or more implementations of the present disclosure. For example, the system 500 may be included in any or all of the server components, or other computing device(s), discussed herein. The system 500 may include one or more processors 510, one or more memories 520, one or more storage devices 530, and one or more input/output (I/O) devices 540. The components 510, 520, 530, 540 may be interconnected using a system bus 550.

The processor 510 may be configured to execute instructions within the system 500. The processor 510 may include a single-threaded processor or a multi-threaded processor. The processor 510 may be configured to execute or otherwise process instructions stored in one or both of the memory 520 or the storage device 530. Execution of the instruction(s) may cause graphical information to be displayed or otherwise presented via a user interface on the I/O device 540.

The memory 520 may store information within the system 500. In some implementations, the memory 520 is a computer-readable medium. In some implementations, the memory 520 may include one or more volatile memory units. In some implementations, the memory 520 may include one or more non-volatile memory units.

The storage device 530 may be configured to provide mass storage for the system 500. In some implementations, the storage device 530 is a computer-readable medium. The storage device 530 may include a floppy disk device, a hard disk device, an optical disk device, a tape device, or other type of storage device. The I/O device 540 may provide I/O operations for the system 500. In some implementations, the I/O device 540 may include a keyboard, a pointing device, or other devices for data input. In some implementations, the I/O device 540 may include output devices such as a display unit for displaying graphical user interfaces or other types of user interfaces.

The features described may be implemented in digital electronic circuitry, or in computer hardware, firmware, software, or in combinations of them. The apparatus may be implemented in a computer program product tangibly embodied in an information carrier (e.g., in a machine-readable storage device) for execution by a programmable processor; and method steps may be performed by a programmable processor executing a program of instructions to perform functions of the described implementations by operating on input data and generating output. The described features may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language, including compiled or interpreted languages, and it may be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Elements of a computer may include a processor for executing instructions and one or more memories for storing instructions and data. Generally, a computer may also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, application-specific integrated circuits (ASICs).

To provide for interaction with a user, the features may be implemented on a computer having a display device such as a cathode ray tube (CRT) or liquid crystal display (LCD) monitor for displaying information to the user and a keyboard and a pointing device such as a mouse or a trackball by which the user may provide input to the computer.

The features may be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system may be connected by any form or medium of digital data communication such as a communication network. Examples of communication networks include, e.g., a local area network (LAN), a wide area network (WAN), and the computers and networks forming the Internet.

The computer system may include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A computer-implemented method executed by a system of one or more computers, the method comprising:
receiving, by the one or more computers and from a user device of a user, a plurality of answers to a first set of questions, each answer in the plurality of answers being associated with one of the questions in the first set of questions and forming a question-answer pair, wherein each answer comprises an answer value within a range of values;
generating an adjacency matrix based on the question-answer pairs, each element of the adjacency matrix representing correlations between two respective question-answer pairs, the correlation being determined based on answer-values of answers in the two respective question-answer pairs;
determining a network graph comprising question nodes and edges, each question node representing a respective question-answer pair and each edge representing correlations between a pair of question nodes, the edges being derived from elements of the adjacency matrix;
identifying one or more clusters of question nodes by applying a community detection algorithm on the network graph;
determining, for each cluster, i) a cluster centrality and ii) a cluster magnitude, the cluster centrality of a cluster being determined based on the edges within the cluster, and the cluster magnitude for the cluster being determined based on answer-values associated with question nodes in the cluster;

ranking the clusters based on the cluster centralities and the cluster magnitudes of the one or more clusters;

selecting a second set of questions for the user, wherein the second set of questions has fewer questions than the first set of questions,
   each question in the second set of questions is associated with a cluster in the one or more clusters, and
   the questions in the second set of questions are selected based on each question's association with a respective cluster and a cluster rank of the respective cluster; and causing the questions from the second set of questions to be presented to the user.

2. The method of claim 1, further comprising:

receiving a user answer to a particular question from the second set of questions;

updating the adjacency matrix, the network graph, and the one or more clusters based on the user answer to provide updated clusters;

ranking the cluster centrality and cluster magnitude of the updated clusters; and selecting a new question to be added to the second set of questions based on the ranking of the updated clusters.

3. The method of claim 2, wherein the new question is selected from one of the updated clusters other than the highest-ranked updated cluster.

4. The method of claim 1, wherein questions associated with answers that have lower differences in their answer-values are more highly correlated than questions that are associated with answers that have greater differences in their answer-values.

5. The method of claim 1, wherein the network graph is a weighted graph, wherein an edge between two question nodes has a respective weight that is calculated based on a difference between the answer-values of answers in question-answer pairs associated with the two question nodes.

6. The method of claim 1, further comprising:

receiving, from the user, user answers to the second set of questions; and determining a health issue for the user based on the user answers to the first set of questions and the second set of questions.

7. The method of claim 6, wherein the health issue is determined based on correlations between symptoms of the health issues and question-answer pairs in the highest ranked cluster.

8. A system comprising:

at least one processor; and a data store coupled to the at least one processor having instructions stored thereon which, when executed by the at least one processor, causes the at least one processor to perform operations comprising:

receiving, from a user device of a user, a plurality of answers to a first set of questions, each answer in the plurality of answers being associated with one of the questions in the first set of questions and forming a question-answer pair, wherein each answer comprises an answer value within a range of values;

generating an adjacency matrix based on the question-answer pairs, each element of the adjacency matrix representing correlations between two respective question-answer pairs, the correlation being determined based on answer-values of answers in the two respective question-answer pairs;

determining a network graph comprising question nodes and edges, each question node representing a respective question-answer pair and each edge representing correlations between a pair of question nodes, the edges being derived from elements of the adjacency matrix;

identifying one or more clusters of question nodes by applying a community detection algorithm on the network graph;

determining, for each cluster, i) a cluster centrality and ii) a cluster magnitude, the cluster centrality of a cluster being determined based on the edges within the cluster, and the cluster magnitude for the cluster being determined based on answer-values associated with question nodes in the cluster;

ranking the clusters based on the cluster centralities and the cluster magnitudes of the one or more clusters;

selecting a second set of questions for the user, wherein the second set of questions has fewer questions than the first set of questions,
   each question in the second set of questions is associated with a cluster in the one or more clusters, and
   the questions in the second set of questions are selected based on each question's association with a respective cluster and a cluster rank of the respective cluster; and causing the questions from the second set of questions to be presented to the user.

9. The system of claim 8, wherein the operations further comprise:

receiving a user answer to a particular question from the second set of questions;

updating the adjacency matrix, the network graph, and the one or more clusters based on the user answer to provide updated clusters;

ranking the cluster centrality and cluster magnitude of the updated clusters; and selecting a new question to be added to the second set of questions based on the ranking of the updated clusters.

10. The system of claim 9, wherein the new question is selected from one of the updated clusters other than the highest-ranked updated cluster.

11. The system of claim 8, wherein questions associated with answers that have lower differences in their answer-values are more highly correlated than questions that are associated with answers that have greater differences in their answer-values.

12. The system of claim 8, wherein the network graph is a weighted graph, wherein an edge between two question nodes has a respective weight that is calculated based on a difference between the answer-values of answers in question-answer pairs associated with the two question nodes.

13. The system of claim 8, wherein the operations further comprise:

receiving, from the user, user answers to the second set of questions; and determining a health issue for the user based on the user answers to the first set of questions and the second set of questions.

14. The system of claim 13, wherein the health issue is determined based on correlations between symptoms of the health issues and question-answer pairs in the highest ranked cluster.

15. A non-transitory computer readable storage medium storing instructions that, when executed by at least one processor, cause the at least one processor to perform operations comprising:

receiving, from a user device of a user, a plurality of answers to a first set of questions, each answer in the plurality of answers being associated with one of the questions in the first set of questions and forming a question-answer pair, wherein each answer comprises an answer value within a range of values;

generating an adjacency matrix based on the question-answer pairs, each element of the adjacency matrix representing correlations between two respective question-answer pairs, the correlation being determined based on answer-values of answers in the two respective question-answer pairs;

determining a network graph comprising question nodes and edges, each question node representing a respective question-answer pair and each edge representing correlations between a pair of question nodes, the edges being derived from elements of the adjacency matrix;

identifying one or more clusters of question nodes by applying a community detection algorithm on the network graph;

determining, for each cluster, i) a cluster centrality and ii) a cluster magnitude, the cluster centrality of a cluster being determined based on the edges within the cluster, and the cluster magnitude for the cluster being determined based on answer-values associated with question nodes in the cluster;

ranking the clusters based on the cluster centralities and the cluster magnitudes of the one or more clusters;

selecting a second set of questions for the user, wherein the second set of questions has fewer questions than the first set of questions,
  each question in the second set of questions is associated with a cluster in the one or more clusters, and
  the questions in the second set of questions are selected based on each question's association with a respective cluster and a cluster rank of the respective cluster; and causing the questions from the second set of questions to be presented to the user.

16. The medium of claim 15, wherein the operations further comprise:

receiving a user answer to a particular question from the second set of questions;

updating the adjacency matrix, the network graph, and the one or more clusters based on the user answer to provide updated clusters;

ranking the cluster centrality and cluster magnitude of the updated clusters; and selecting a new question to be added to the second set of questions based on the ranking of the updated clusters.

17. The medium of claim 16, wherein the new question is selected from one of the updated clusters other than the highest-ranked updated cluster.

18. The medium of claim 15, wherein questions associated with answers that have lower differences in their answer-values are more highly correlated than questions that are associated with answers that have greater differences in their answer-values.

19. The medium of claim 15, wherein the network graph is a weighted graph, wherein an edge between two question nodes has a respective weight that is calculated based on a difference between the answer-values of answers in question-answer pairs associated with the two question nodes.

20. The medium of claim 15, wherein the operations further comprise:

receiving, from the user, user answers to the second set of questions; and determining a health issue for the user based on the user answers to the first set of questions and the second set of questions.

* * * * *